United States Patent [19]

Meserol et al.

[11] 4,411,518

[45] Oct. 25, 1983

[54] APPARATUS FOR USE IN QUALITATIVE DETERMINATION OF IMMUNOLOGICAL REACTIONS

[75] Inventors: Peter M. Meserol, Montville; Jesse L. Acker, Rockaway, both of N.J.

[73] Assignee: Gamma Biologicals, Inc., Houston, Tex.

[21] Appl. No.: 97,195

[22] Filed: Nov. 26, 1979

Related U.S. Application Data

[62] Division of Ser. No. 835,996, Sep. 23, 1977, Pat. No. 4,197,088.

[51] Int. Cl.³ .................... G01N 21/03; G01N 33/48
[52] U.S. Cl. ...................................... 356/39; 356/244; 356/246; 356/440
[58] Field of Search ............... 356/244, 246, 39, 440; 350/95; 250/576; 73/426, 64.1; 422/104, 102, 73; 424/12

[56] References Cited

U.S. PATENT DOCUMENTS

| | | | |
|---|---|---|---|
| 3,390,229 | 6/1968 | Williams | 356/39 X |
| 3,395,210 | 7/1968 | Lenahan et al. | 23/230 B |
| 3,463,614 | 8/1969 | Leslie | 23/230 B |
| 3,520,609 | 7/1970 | Lion | 250/574 X |
| 3,521,964 | 7/1970 | Wilks, Jr. | 356/246 |
| 3,565,537 | 2/1971 | Fielding | 350/95 X |
| 3,617,222 | 11/1971 | Matte | 23/230 B |
| 3,770,380 | 11/1973 | Smith | 424/12 X |
| 3,803,299 | 4/1974 | Nouel | 23/230 B X |
| 3,819,271 | 6/1974 | Beug | 356/39 |
| 3,826,613 | 7/1974 | Parikh et al. | 23/230 B |
| 3,829,216 | 8/1974 | Persidsky | 350/96 X |
| 3,905,767 | 9/1975 | Morris | 424/12 X |
| 3,915,640 | 10/1975 | Turner et al. | 23/230 B |
| 3,932,141 | 1/1976 | Beall et al. | 23/230 B |
| 3,967,901 | 7/1976 | Rodrigues | 250/574 X |
| 3,984,533 | 10/1976 | Uzgiris | 424/12 |
| 3,990,851 | 11/1976 | Gross | 424/12 X |
| 4,003,988 | 1/1976 | Hoff et al. | 23/230 B X |
| 4,027,973 | 6/1977 | Kaye | 250/574 X |
| 4,043,669 | 8/1977 | Gehatia | 356/246 X |
| 4,050,895 | 9/1977 | Hardy | 424/12 X |
| 4,052,010 | 10/1977 | Baker et al. | 23/230 B X |
| 4,080,264 | 3/1978 | Cohen | 424/12 X |
| 4,097,149 | 6/1978 | Aladjem | 356/72 |
| 4,118,192 | 10/1978 | Sawai | 424/12 |
| 4,136,953 | 1/1979 | Klein | 250/574 X |

*Primary Examiner*—Vincent P. McGraw

[57] ABSTRACT

An apparatus is provided for use in qualitative and quantitative determinations of agglutination in immunoreactive systems. The apparatus comprises a carriage assembly having a plurality of spaced, axially-disposed compartments for receiving image cells which are uniquely designed for holding the biological fluid test specimen and the reagent therefor. Means are provided for partially lifting each image cell successively out of its compartment and into an optical path. A monochromatic light source directs beams of radiant energy through the reaction zone in each image cell and the light beams transmitted through the reaction zone are focused, by means of an imaging lens, on the surface of an image sensor such as a "Charge-Coupled Device". The dark areas formed on the image sensor are measured electronically and also displayed on a display cathode ray tube.

30 Claims, 17 Drawing Figures

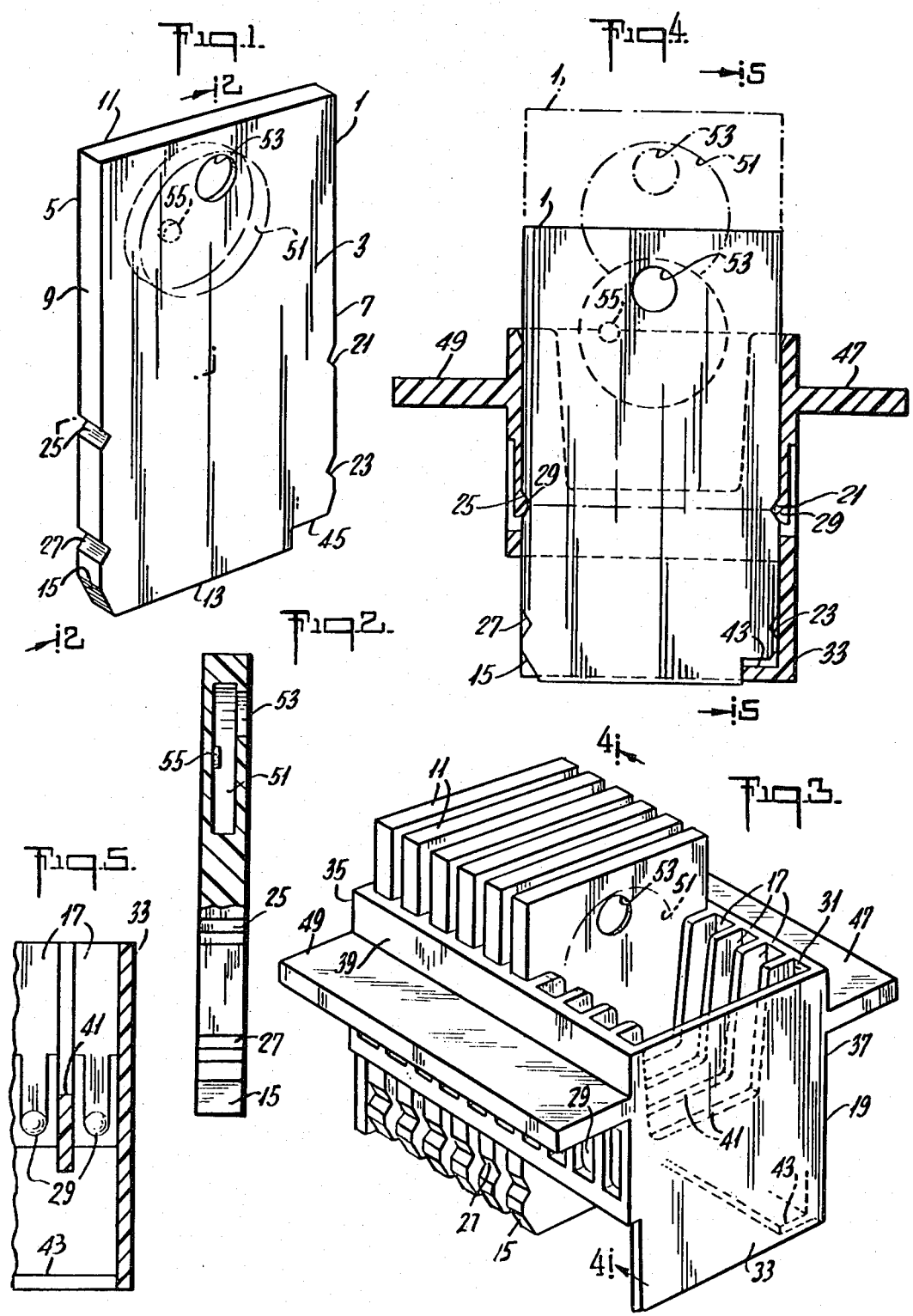

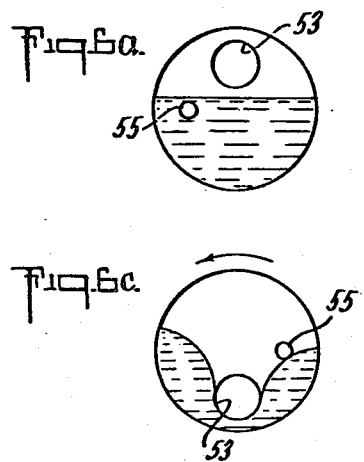
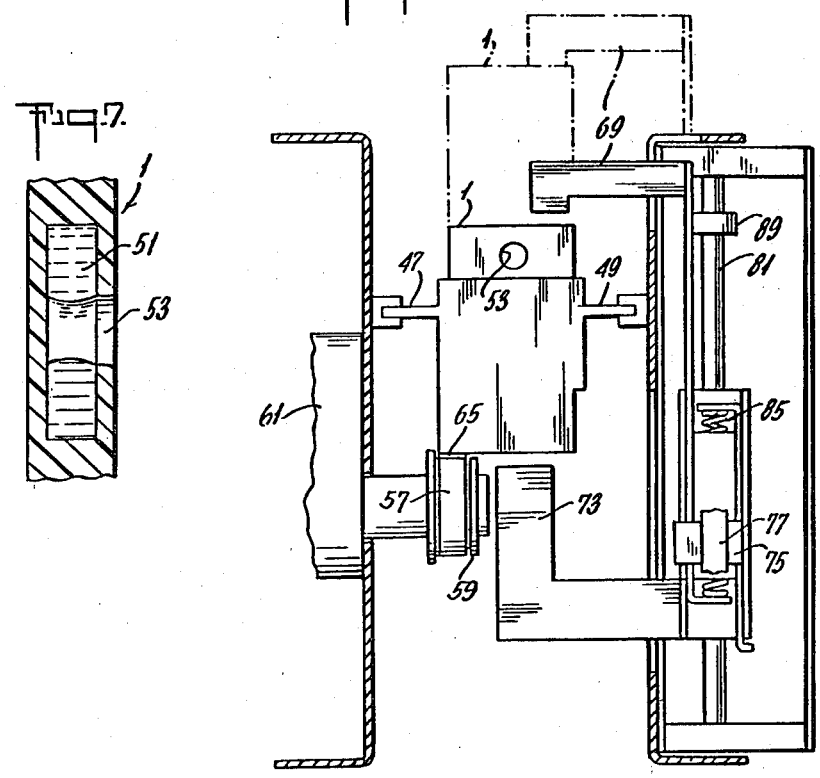

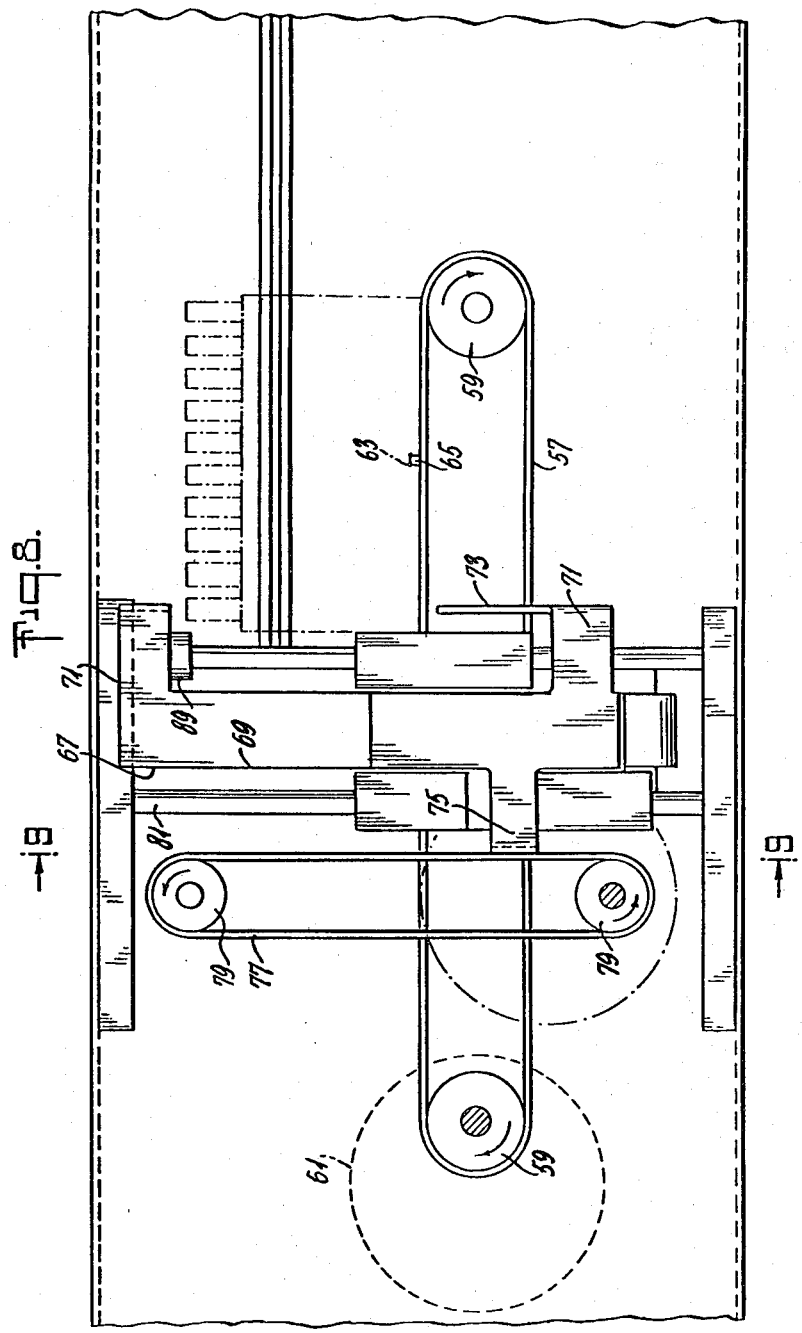

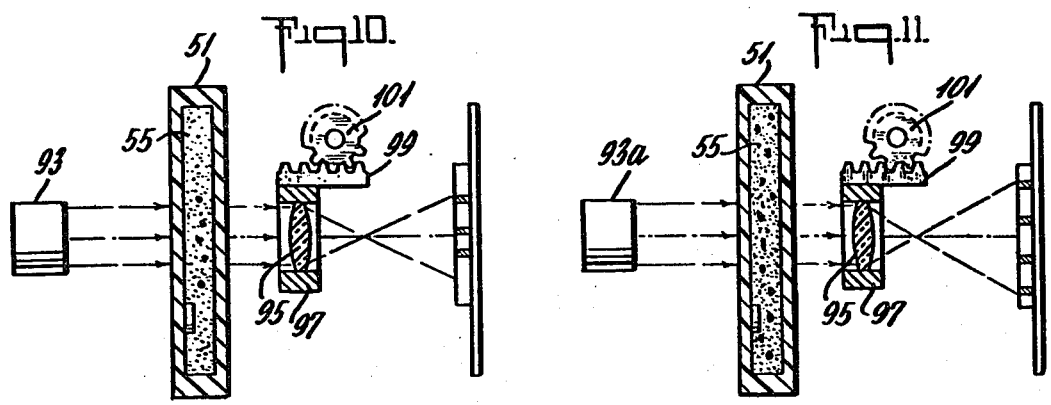
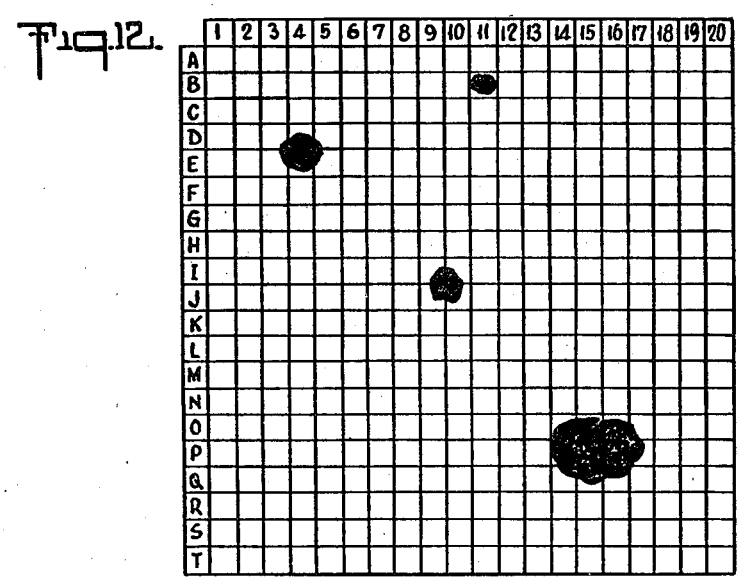
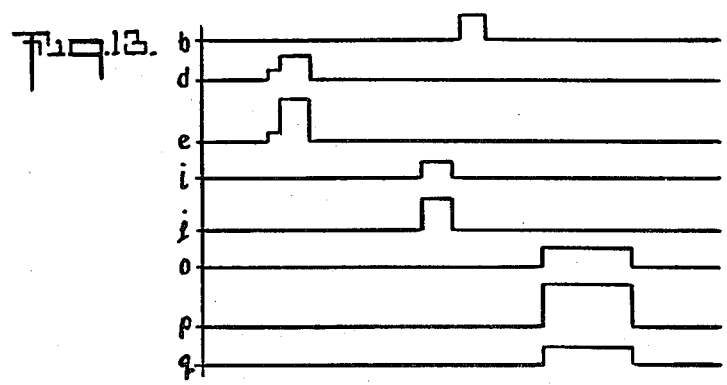

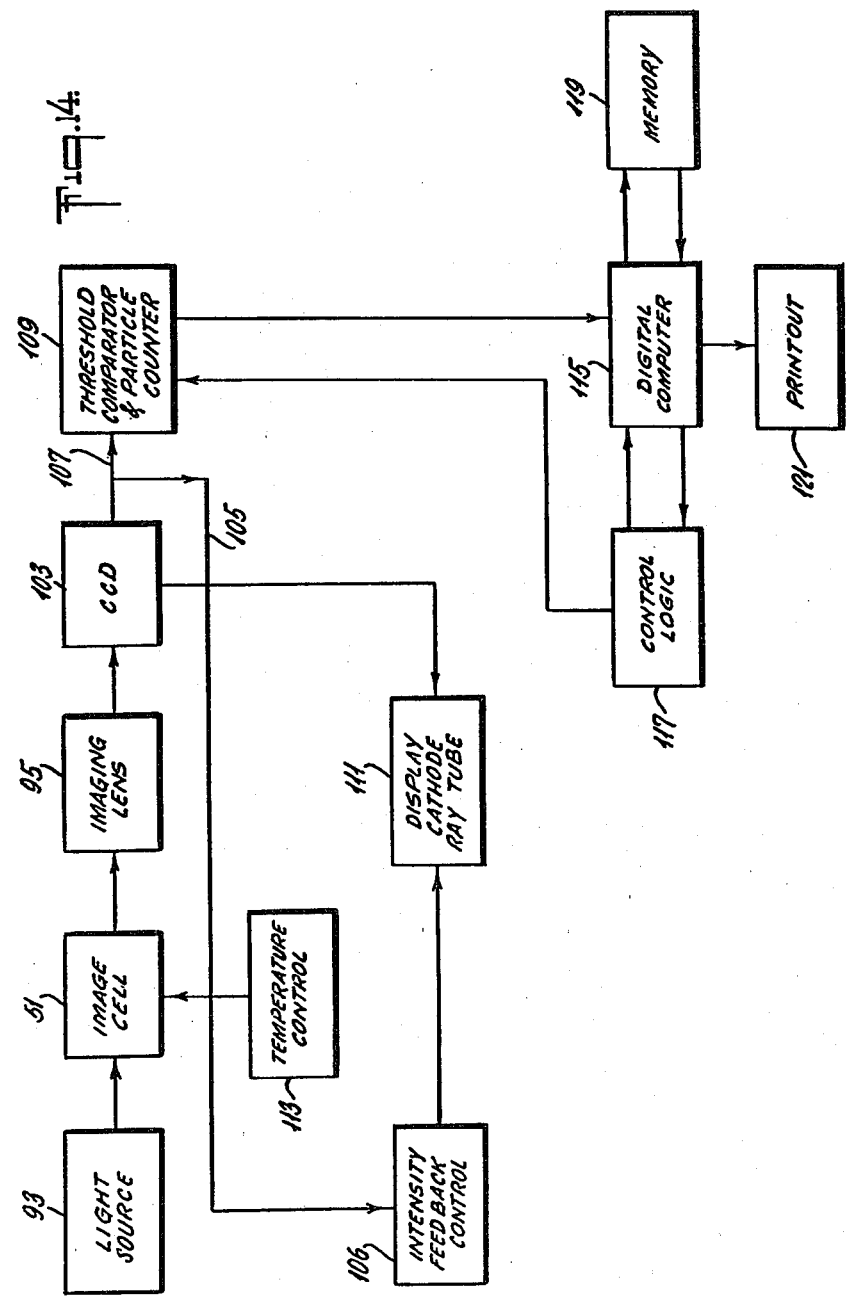

APPARATUS FOR USE IN QUALITATIVE DETERMINATION OF IMMUNOLOGICAL REACTIONS

This is a division of application Ser. No. 835,996, filed Sept. 23, 1977 now U.S. Pat. No. 4,197,088.

BACKGROUND OF THE INVENTION

1. Field of Invention

This invention relates to immunoassay procedures and it is particularly related to a method of qualitative and quantitative determination of immunological reactions. More specifically, the present invention is concerned with the application of an electro-optical imaging technique for quantification of the degree of agglutination which is present in an immunological reaction system, and the determination of the concentration of the immunoreactive components which cause the agglutination in such system. The invention is also concerned with the apparatus employed in the practice of this method.

2. The Prior Art

The assay of drugs in biological fluids has attracted considerable attention in recent years and therapeutic monitoring of drugs has achieved considerable clinical significance and has stimulated the development of new assay systems and techniques. Assay systems involving the use of antigen, haptens, or antibodies labeled with an enzyme have recently been applied to measurement of substances in various biological fluids. See. G. Brian Wisdom, "Enzyme-Immunoassay", Clinical Chemistry, Vol. 22, No. 8 (1976), pp. 1243–55. These assay systems are known as enzyme immunoassay, generally abbreviated as "EIA" and enzyme-linked immunoassay, abbreviated as "ELISA". Other techniques include radio-immunoassay (RIA) which involves producing hapten protein conjugates, and radiolabelling at specific sites on the drug molecule. See Alan Broughton and James E. Strong, "Radioimmunoassay of Antibiotics and Chemotherapeutic Agents," Clinical Chemistry, Vol. 22, No. 6 (1976), pp. 726–32, and R. Cleeland et al, "Detection of Drugs of Abuse of Radio Immunoassay: A Summary of Published Data and Some New Information." Clinical Chemistry, Vol. 22, No. 6 (1976), pp. 713–25.

Prior to the development of the various recent assay techniques, the presence of antigen/antibody complexes were usually detected visually by the naked eye. However, the naked eye could not detect or differentiate marginal, but clinically meaningful reactions and, therefore, the results often had limited clinical significance. Even microscopic examination afforded limited clinical information since it could not provide quantitative results.

While EIA techniques, in general, provide specific and highly sensitive methods for identification and quantification of wide ranges of substances, they suffer from several disadvantages and limitations. These techniques are generally less sensitive than RIA and they are more susceptible to interference. Additionally, the determination of end point (the initial velocity of enzymatic reaction) is more difficult than in RIA techniques, and, moreover all EIA techniques, except homogeneous EIA, require separation of the bound molecules from the free labeled molecules. However, the number of separation methods which can be applied are usually limited.

The RIA techniques, on the other hand, require the production of a specific antibody and the development of a suitable radioactive labeled compound. The application of this technique requires extreme care and expertise due to hazard of radiation and the radiation damage may even adversely affect the immunochemical reactivity of the labelled substance.

Other known assay systems include spin-immunoassay in which known amounts of antibodies to the drug to be detected are mixed with an analog of the drug that has been labeled with nitroxide label (spin label) and the specimen of biological fluid is then added to this mixture. The drug concentration in the unknown sample is then determined by electron spin measurement. See Simon L. Sharpe, "Quantitative Enzyme Immunoassay: Current Status," Clinical Chemistry, Vo. 22, No. 6 (1976), pp. 733–38.

Still other assay techniques are available which include the attachment of antibodies to fluorescent compounds capable of emitting light when excited by illumination of specific wavelengths; and the utilization of opaque, colloidal particles such as latex spheres, glass and ceramic spheres, kaolin, carbon and charcoal particles, as well as animal blood components, typically erythrocytes, and attaching the antigen/antibody thereto.

In the aforementioned immunoassay techniques, the labeled component of an antigen/antibody reaction binds to its complementary site, and the amount bound depends upon the concentration of the other component, and if one of these concentrations is varied, there will be a concomittant change in the distribution of the labelled component between the bound and unbound fractions. The properties of the labels determine its distribution and a calibration curve can be constructed relating the concentration of the variable (unlabeled) component to the labeled component. Presently, this is accomplished by the removal of either the bound or unbound fraction by means of solid-phase absorbtion in test tubes or plastic beads, centrifugation, repeated resuspension and washing steps. Although, these procedures provide a curve defining the relationship between the bound and unbound fractions, they are tedious, cumbersome and require complicated equipment. Additionally, EIA, RIA and spin immunoassay usually require the introduction into the reactive system labels which, while not immunoreactive, they may adversely affect the immunoreactivity of the system through the chemical or radioemissive activity which permits their use as the labels.

The classical visual indicators of immunoreactivity do not suffer from the disadvantages of EIA, RIA and spin immunoassay procedures since they do not require phase separation and removal of the components from the immunoreactive system, nor do they require the introduction of labels which interfere with or modify the immunoreactivity of the system under consideration. Rather, they are based on redistribution of the opaque particles from a uniform non-agglutinated state to an agglutinated state. Since each particle serves as the label for numerous immunoreactive protein molecules, a number of labeled particles are agglutinated to form a characteristic microscopic agglutination texture, which is read qualitatively by visual inspection. However, this procedure does not lend itself to quantitative measurement and hence it is likewise of very limited clinical significance.

There are also numerous patents which relate to different methods and approaches for the detection of agglutination reactions. Thus, U.S. Pat. No. 3,074,853 (Brewer) discloses a method and means for carrying out immunological reactions by forming and spreading a mixture of a finely divided solid and two liquids to be tested for antigen/antibody reaction in a test spot on an opaque surface of contrasting color with respect to said solid. The test spot is then examined visually.

U.S. Pat. No. 3,520,609 (Lion) discloses a method for detecting agglutination reactions which comprises scanning samples of the specimen by a beam of energy (e.g., light or electrons). Substantial agglutination establishes significant demarcations in the scanned zone between the agglutinated cells and the surrounding area, and these demarcations modulate the scanning beam as it crosses them, causing a change in rate in the signal produced thereby. A second signal is derived from the rate of change of the signal generated by the beam of light, integrated during a predetermined period and the integrated value is compared with a predetermined standard, corresponding to substantial agglutination to determine if such agglutination has occurred in the reaction area.

U.S. Pat. No. 3,819,271 (Beug) describes a method and an apparatus for the measurement of cell agglutination in a carrier liquid. According to the procedure described in this patent, a carrier liquid having cells suspended therein is enclosed in a container which is moved in a circular path and a beam of light is passed through the suspension. The degree of agglutination of the cells is determined from the amount of light "scattered" by passage through the suspension.

U.S. Pat. No. 3,984,533 (Uzgiris) describes an electrophoretic method of detecting antigen/antibody reactions, and U.S. Pat. No. 3,990,851 (Gross et al) describes a process and a device for measuring antigen/antibody reactions by passing a laser light through the reaction mixture and measuring the light "scattered" in the forward direction.

U.S. Pat. No. 3,905,767 (Morris et al) describes a process for qualitative or quantitative measurement of antigen or antibodies with an antigen/antibody reaction in which a "precipitate" is formed. This patent also relies on measuring the extent of light "scattered" by the precipitate when a light beam is projected therethrough.

The methods and apparatus described in the aforementioned patents, and other prior art patents, all require detection of the agglutination reaction by photometric means such as measurement of light scatter, or turbidimetry or opacimetry. Consequently, the measurements are subject to clinically significant errors due to the color or inherent cloudiness of the biological fluid under examination. Moreover, the procedure described in all the aforementioned patents, save for Beug, supra, suffer from uneven distribution of reactant indicators which causes statistical errors upon inspection by automatic means and difficulty in interpretation by manual techniques.

Thus, there is a long-felt need for an assay procedure for the detection and quantification of immunological reactions which is simpler and more rapid to carry out, and which provides clinically more significant information without the difficulties and limitations which are inherent in, or associated with, the currently available immunoassay techniques.

It is therefore an object of this invention to provide an immunoassay procedure, and an apparatus for carrying out the same, for the detection and quantification of immunological reactions.

It is a further object of this invention to provide an immunoassay procedure which provides clinically more significant information as compared with the currently available immunoassay techniques and systems.

It is still a further object of this invention to provide an immunoassay system and procedure in which the detection and quantification of immunological reactions may be carried out more rapidly and more accurately than the prior art systems and procedures.

It is yet another object of this invention to provide an immunoassay procedure which is non-invasive and which does not require separation of the bound fraction from the unbound fraction.

It is still a further object of this invention to provide an immunoassay technique and system capable of extracting a greater proportion of the information available from the labeled components.

It is also an object of this invention to provide a uniquely designed, disposable, planar reaction imaging cell in which the immunological reaction is carried out.

It is a further object of this invention to provide a holder for securing the reaction imaging cell in the apparatus of this invention during image analysis of the reactants in the image cell.

The foregoing and other objects of this invention will become more apparent from the ensuing detailed description taken in conjunction with the accompanying drawings, wherein like reference numerals are employed to designate like parts.

BRIEF DESCRIPTION OF THE DRAWINGS

FIG. 1 is a perspective view of the reaction image cell which is employed in the practice of this invention;

FIG. 2 is a view taken along the line 2—2 of FIG. 1;

FIG. 3 is a perspective view of the carriage assembly for the image cells, constructed in accordance with this invention;

FIG. 4 is a view taken along the line 4—4 of FIG. 3;

FIG. 5 is a view taken along the line 5—5 of FIG. 4;

FIGS. 6a–6d are schematic front views illustrating the respective positions of the reaction cell in each image cell during rotation about is central axis in order to effect mixing and even distribution of the reactants;

FIG. 7 is a sectional view taken along the line 7—7 of FIG. 6a illustrating the toroidal meniscus which is formed in the fill port of the reaction image cell durings its rotation;

FIG. 8 is a schematic view, partly in elevation, illustrating so much of the apparatus of this invention as is required to show both the vertical displacement of each image cell and the lateral displacement of the carriage assembly in accordance with the method of this invention;

FIG. 9 is a view taken along the line 9—9 of FIG. 8;

FIGS. 10 and 11 are schematic representations of the imaging process whereby images of agglutinated indicator particles in the fluid suspension within the reaction cells are formed on an image sensor;

FIG. 12 is a front view of the image sensor on which images of agglutinated particles are formed;

FIG. 13 is a graphic illustration of the electronic signals corresponding to the agglutinated areas on the image sensor, and FIG. 14 is a functional block diagram of the electro-optical method and system employed in the practice of this invention.

SUMMARY OF INVENTION

A unique apparatus and a novel method are provided for the detection and quantification of the immunoreactive components of immunoreactive systems. The apparatus comprises a carriage assembly defined by side panels and front and rear panels, and a plurality of spaced, axially disposed compartments between the side panels. An image cell, uniquely designed to carry out this invention, is inserted into and retained in each of the compartments. Each image cell is made from a pair of opposed, parallel, planar surfaces, each having a generally circular groove so that when said surfaces are bonded together to form a unitary structure, said circular grooves define a reaction cell. One of said circular grooves is provided with a fill port through which the fluid specimen and the reagent are introduced into the reaction cell.

The apparatus is also provided with a means, such as a caliper member, which is adapted to be inserted into said compartments for partially lifting the image cell therefrom and bring it into an optical path such as beams of radiant energy emanating from a monochromatic light source, and an imaging lens is employed to focus the light beams transmitted through the reaction cell on the surface of an image sensor such as a Charge-Coupled Device.

The method comprises pipetting the fluid biological test specimen and a reagent (a substantially opaque, colloidal particle, e.g., latex spheres) into the reaction cell through the fill port, evenly mixing, and incubating the reaction mixture to form agglutinated particles and transilluminating the contents of the reaction cell. The light transmitted therethrough is imaged on the surface of the image sensor where dark areas appear corresponding to the agglutinated particles in the reaction cell. The total dark imaged area is then measured, preferably by electronic means.

This procedure is repeated for test specimen with known antibody concentrations and the resultant dark areas are plotted against these concentrations. The concentration of the immunoreactive component of the unknown test speciment is then obtained from this plot.

DETAILED DESCRIPTION OF THE INVENTION

In accordance with this invention, there is provided a unique method, and an apparatus, for carrying out immunological reactions and for qualitative and quantitative determinations of immunoreactive components of the reaction system. The unique method of this invention contemplates the application of electro-optical imaging techniques to an aliquot portion of the immunoreactive system, and cartographic analysis of the optical images formed on an image sensor. Thus, the degree of agglutination in the immunological reaction medium may be quantified and related to the concentrations of immunoreactive components (i.e., antigens and antibodies) which cause the agglutination.

Referring now to the drawings, and with particular reference first to FIG. 1, there is shown an image cell generally designated as 1 for carrying out the immunological reactions, which is uniquely designed for use in the electro-optical system of this invention. The image cell 1 comprises two opposed, parallel, planar surfaces 3 and 5 which are suitably bonded together, preferably by ultrasonic means, to form a unitary structure defined by side edges 7 and 9, top and bottom edges 11 and 13, respectively. The side edges 7 and 9 may be slightly tapered and side edge 9 is chamfered at its lower end such as at 15 for conveniently inserting the image cells in their respective compartments 17 of the carriage assembly 19 as shown in FIG. 3.

Side edges 7 and 9 of the image cell each include a pair of detents or notches such as shown at 21, 23, 25 and 27 which are adapted to engage with corresponding resilient protuberations 29 formed in the walls or channels 31 of each compartment 17 when the image cells are inserted therein.

As illustrated in FIG. 3, the carriage assembly 19 is defined by front and rear panels or walls 33 and 35, and side panels or walls 37 and 39. A plurality of generally U-shaped partition walls 41 are spaced along the principal axis of the carriage assembly 19, and they are suitably bonded or affixed to the side walls 37 and 39 thereby defining the respective compartments 17 in the carriage assembly.

The side panel or wall 39 is partial wall extending slightly over one-half the height of each compartment, and side panel or wall 37 is conveniently shouldered internally at its lower end as at 43 so that when each image cell is fully inserted in its respective compartment, the ear portion 45 formed in the bottom edge 13 of the image cell rests on said shoulder 43. This construction, together with the engagement of the notches 21, 23, 25 and 27 with their corresponding protuberations in channels 31 prevent the image cells from dropping through said compartments.

As is further shown in FIGS. 3 and 4, the carriage assembly 19 is also provided with the lateral flange members 47 and 49 which can be gripped between the fingers for conveniently inserting the carriage assembly in the apparatus of this invention, or removing it therefrom.

Referring once again to FIG. 1, each of the opposing faces of the two planar surfaces 3 and 5 is provided with a generally circular groove which, when the two surfaces are bonded together as aforesaid, define the reaction cell 51 in which the immunological reaction is carried out. A fill port 53 is pierced in the circular groove provided in the planar surface 3 for the introduction of the reagent and the biological fluid in the reaction cell, and a focus target 55, e.g., a generally round cylindrical member, is molded on the circular groove on the inner face of the planar surface 5 in the reaction cell 45 in order to allow the optical system to focus on the plane which is halfway in the reaction cell.

The two planar surfaces 3 and 5 may be made of glass or suitable plastic material such as polystyrene. Although both surfaces may be made of transparent material, one may be transparent and the other translucent, in which case the planar surface 3 is made of a translucent material while the planar surface 5 is made of a transparent substance.

To introduce the reagents and the biological fluid specimen into the reaction cell, and with particular reference to FIGS. 3 and 4, the side edges 7 and 9 of each image cell are gripped between the fingers and pulled out of its compartment until the notches 21 and 25 engage with their corresponding protuberations in the channels 31. The particular reagent and the biological fluid are sequentially introduced into the reaction cell 51 through the fill port 53, using a pipette or some other suitable means. The image cell is then pushed all the way down in its compartment and the next image cell is filled with reagent and biological fluid as aforesaid. A plurality of reaction image cells are thus filled with the reagent and the desired biological fluid to be tested.

After the reagent and the biological fluid have been introduced into the reaction image cells as aforesaid, they are mixed and evenly distributed by slow rotation of the carriage assembly about its axis of rotation. FIGS. 6a–6b illustrate the respective positions of each image cell during the rotation of the carriage assembly. Egress of the fluid from the reaction image cell 51 is prevented by the formation of a so-called "toroidal" meniscus around the fill port 53 (FIG. 7) during such rotation.

The carriage assembly 19 may be rotated manually, although the apparatus of this invention is designed to facilitate automatic rotation until the desired degree of mixing and uniformity has been achieved. The speed of rotation of the carriage assembly may vary provided, however, that the surface tension of the liquid meniscus is at no time exceeded by the centrifugal force of the fluid in each reaction image cell. As a practical matter, slow rotation of the carriage assembly for few minutes is adequate to obtain proper mixing and even distribution of the reactants in each reaction image cell.

Prior to the imaging process which will hereinafter be defined, the contents of the reaction cells are incubated under suitable incubating conditions which will vary depending on the requests and the biological fluids which are employed. Generally, the temperature of the fluid in each reaction cell during incubation is maintained at about 25° C. to about 50° C. for about 5 to 15 minutes. The incubation may be carried out while the image cells are loaded in the carriage assembly in a suitable chamber in the apparatus of this invention, or in a separate chamber, if so desired.

The reagents which are suitable in the practice of this invention are substantially opaque colloidal substances such as for example, charcoal, latex spheres, glass or ceramic spheres, kaolin clays, polystyrene beads, mammalian erythrocytes, etc., having a particle size of from about 1 micron to about 5 microns, or somewhat larger. Since latex and charcoal granules exhibit a high degree of opacity and are readily available, they are generally used as the reagent of choice in the practice of this invention, although latex is preferred.

Referring now to FIGS. 8 and 9, the carriage assembly 19 is disposed on a conveyor 57 which is trained over the pulleys 59 which are connected to and driven by the motor 61. The conveyor belt 57 has a lug 63 for engagement with protuberations 65 on the carriage assembly as it is sequentially advanced into position after each imaging process.

In order to lift each image cell out of its respective compartment and bring it into the optical path, the apparatus of this invention is equipped with a caliper member generally designated as 67 which includes an upper caliper segment 69 and a lower caliper segment 71. The lower caliper segment 71 has an integral vertically projecting arm 73 adapted to be inserted into each compartment in the carriage assembly to push each image cell up and out into the optical path. The lower caliper segment has a lateral arm 75 which is fixed to a belt 77 which is trained over the pulleys 79 which are connected to and driven by a motor 83.

The upper and lower caliper segments are attached to a guide rod 81 and are normally fixed to and biased together by means of the spring loaded member 83 which includes the spring elements 85 and 87. The upper caliper segment 69 is retained above the image cells by means of the stop member 89 which is installed on the guide rod.

In order to bring each image cell into the optical path, the motor 81 is activated by a switch (not shown) thus causing the belt 77 to travel in an upward vertical path. This will bring the vertically projecting part 73 of the lower caliper segment into engagement with the lower edge of the image cell and, as the belt continues its travel, forces the image cell up and against the upper caliper segment 69, and partially out of the carriage assembly into the optical path as illustrated in FIG. 9.

After imaging the contents of the reaction cell, the image cell is returned to its original position in its compartment by reversing the direction of travel of the belt 77. Thereafter, the motor 61 is activated thereby driven the belt 57 in the direction of the arrows in FIG. 9. When the lug 63 engages the next protuberation in the carriage assembly corresponding to the next compartment, the motor 61 is automatically shut off and motor 81 is activated to bring the next image cell into the optical path for imaging. This operation is continued for imaging as many image cells as desired.

As shown in FIGS. 10 and 11, the electro-optical system of the apparatus of this invention includes a source of radiant energy such as a monochromatic light source 93 or 93a from which a beam of monochromatic light impinges upon the image cell 51 to transilluminate the content of the reaction cell 55. The area which is transilluminated by the light beams contains a polydispersed even distribution of the labeled latex particles which is representative of the entire section media within the reaction cell.

The depth of the reaction cell 55 must be minimal in order to concentrate a substantial proportion of the indicator particles in the focus plane of the optical system which is caused to correspond with the image plane from where all information is derived.

The light beams emanating from the light source 93 may be collimated and condensed by means of a condensing lens (not shown) and the light transmitted through the reaction cell 55 is passed through an image-forming lens 95 of proper diopter. The image lens 95 is mounted within a focusing means 97 which is operably connected by a rack and pinion arrangement 99 and 101 for adjusting the focusing lens. The light beams transmitted through the focusing lens 95 impinge upon the surface of an image sensor 103 on which images of the agglutinated indicator particles are formed.

The image sensor 103 is a Charge-Coupled Device, abbreviated in the trade as "C.C.D." and maybe of the type described by Gilbert F. Amalio in an article entitled "Charge-Coupled Device", Scientific American (February, 1974), pages 23-33. The C.C.D. comprises a silicon grid which consists of 10,000 photosensor elements arrayed in 100×100 rectangular sections or wells, and metal contacts around the borders of the grid for connecting to the metal connectors. When light falls on the surface of the silicon grid, the radiation is absorbed and electron charges are removed in a quantity proportional to the amount of incident light.

Thus, in accordance with this invention, the opaque indicator particles in the biological fluid within the reaction cell 53 are transilluminated and imaged on the photosensitive surface of the C.C.D. The magnification of the optical system is adjusted so that the images of the non-agglutinated particles are smaller in size than the area of each photosensitive element (picture element or pixel). Since the electrical outputs from the photosensitive elements are proportional to the amount of light impinging on their surfaces, if a non-agglutinated particle image is smaller than one pixel, its electrical output will be less than the electrical output corresponding to a fully shadowed pixel. Accordingly, a threshold rejection criteria can be set up to reject all image areas whose electrical outputs are less than a pre-determined threshold level, such as the non-agglutinated particles, i.e., particles which even though they are in close proximity to each other, they are not in total contact, and hence permit the passage of some light therethrough.

When several indicator particles agglutinate into a large aggregate or clump, the resulting image will shadow several pixels as shown in FIG. 12 and, due to tight clumping of the agglutinated particles in all three dimensions, they will appear darker than a single particle. After forming images of the agglutinated particles as aforesaid, the C.C.D. is scanned electronically row by row. Any pixel which sees an imaged section which is darker than the threshold level will cause an electrical (voltage) output which is a function of the image density of the agglutinated particles. This is graphically illustrated in FIG. 13 which shows the electrical outputs corresponding to the agglutinated particles on the photosensitive surface of the C.C.D. shown in FIG. 12.

The method of this invention is uniquely suited to determine such disease states as syphillis, hepatitis, etc. In general, the method comprises coating the indicator (latex) particles with the disease-associated antigen. The antigen may be attached to the surface of the latex by absorption, adsorption, chelation or other known prior art techniques and the complementary immunoreactive component is present in the analyte, i.e., the biological test specimen, e.g., blood sera. When the analyte is added to the latex-coated particles, the reaction between the antigen and antibody is believed to form a physico-chemical complex which results in agglutination of the latex particles. The degree of agglutination is dependent upon the number of available complementary sites and the reaction proceeds until all antigen sites have united with the antibodies in the analyte.

Thus, clumps, i.e., agglutinated particles of different sizes are formed in the reaction media, the number and size of which are proportional to the relative concentrations of antigen/antibody in the analyte and the indicator particles. After transilluminating the reaction cell and forming images of the agglutinated particles, the imaged areas are quantified (electronically) and the total area is obtained which is a function of the concentration of the antibody in the analyte.

The foregoing method may be used for qualitative determination of an unknown specimen. Thus, the procedure heretofore described may be repeated for a reference sample and the total dark imaged areas are compared to determine the nature of the unknown specimen.

In order to determine the concentration of the immunoreactive component in the unknown biological specimen, the foregoing procedure is repeated for at least two control specimen of known, but different antibody concentrations, one of which may be a negative control (a serum containing no antibodies). The total dark imaged areas of the control specimen are then related to their respective concentrations. The antibody concentration of the unknown specimen may be determined from the total dark imaged area obtained for the unknown specimen, and the relationship of the total dark imaged areas of the control specimen and their concentrations.

The electro-optical system of this invention may be conveniently described with reference to the block diagram shown in FIGS. 14. As shown in this diagram, the image cell 51 is transilluminated by monochromatic light beams emanating from the light source 93. The light beams transmitted through the image cell are focused on the C.C.D. 103 by means of the imaging lens 95. The output from the C.C.D. follows two paths; a first path 105 for providing averaged data to the intensity feedback control 106 and a second path 107 which provides data for the determination of particle size and their frequency of occurence.

The second path 107 feeds into a threshold comparator and particle counter 109 which screens the non-agglutinated particles on the basis of both intensity and particle size. The comparator 109 passes tightly clumped particles (i.e., agglutinated particles) which produce very dark images on the C.C.D. 103 as contrasted to the grey images which result from non-agglutinated particles, and further serves to eliminate counts resulting from out-of-focus particles.

A display cathode ray tube 117 serves to assemble the serial output data from C.C.D. 103 into an image of the reaction field, thus displaying a pictorial illustration of the test sample and a visual feedback for determining the performance of the system.

A temperature control unit 113 monitors and controls the temperature of the image cells' contents at a pre-determined optimum level.

The system illustrated in FIG. 14 also comprises a digital computer 115 and a control logic 117 for monitoring and controlling the major functions of the instrument and various assemblies. A memory section 119 serves to store the computer output and a printout section 121 prints the results of the computer.

The invention will now be illustrated by the following two examples. It must be understood, however, that three examples are not intended to limit the scope of this invention or its applicability to other disease states.

EXAMPLE I

This example describes the applicability of the method and apparatus of this invention for syphilis.

60 microliters of RPR (Rapid Plasma Reagent) charcoal antigen suspension (HWD), a government supplied reagent made by the Veneral Disease Reagent Laboratory, was pipetted into each of 30 image cells loaded in three magazines as hereinbefore described. Additionally 40 microliters of the following control sera (taken from patients with syphilis) was introduced into each of cells 1–4.

| Cell No. | STD Sera | (1)<br>RPR Card Titer |
|---|---|---|
| 1 | Strongly reactive | 8 |
| 2 | Moderately reactive | 4 |
| 3 | Weakly reactive | 1 |
| 4 | Non-reactive | 0 |

(1) For detailed description of HWD and RPR, see Brewer's U.S. Pat. No. 3,074,853, supra.

The remaining 26 image cells were each charged with additional 40 microliters of the suspected patient sera, and the image cells were incubated by slowly rotating the magazine assemblies at a temperature of 30° C. for eight minutes. The degree of agglutination in each cell was then determined by the apparatus and method hereinbefore described and the results obtained are shown in Table I below.

TABLE I

| Sample Number | Machine Score in Agglutination Units (Area) | Manual Card Score |
|---|---|---|
| 1 (control) | 1500 | +8 |
| 2 (control) | 945 | +4 |
| 3 (control) | 125 | +1 |
| 4 (-control) | 45 | — |
| 5 | 199 | +1 |
| 6 | 45 | — |
| 7 | 59 | — |
| 8 | 42 | — |
| 9 | 37 | — |
| 10 | 32 | — |
| 11 | 998 | +4 |
| 12 | 38 | — |
| 13 | 39 | — |
| 14 | 54 | — |
| 15 | 76 | — |
| 16 | 21 | — |
| 17 | 94 | — |
| 18 | 22 | — |
| 19 | 450 | +2 |
| 20 | 1495 | +8 |
| 21 | 36 | — |
| 22 | 29 | — |
| 23 | 42 | — |
| 24 | 59 | — |
| 25 | 65 | — |
| 26 | 32 | — |
| 27 | 54 | — |
| 28 | 1315 | — |
| 29 | 21 | +8 |
| 30 | | — |

As indicated in Table I, the various scores can be compared to the control samples in order to determine the strength of the disease in the test specimen. Thus, for example, cell no. 5 indicates a weakly reactive condition, and hence, a weak disease state; cell nos. 6-1 indicate absence of syphilis; cell no. 11 indicates a moderate state and cell nos. 20 and 28 suggest highly diseased conditions. Moreover, the results obtained can be quantified in terms of percentage of the positive control as follows:

$$\frac{\text{Machine Score}}{1500} \times 100$$

Thus, for example, the machine score of 998 for cell no. 10 means that the suspected specimen concentration is 998/1500×100 or 66.53 percent of the positive control in cell no. 1. Accordingly, once the concentration of the positive control is known, the degree of diseased state in the test speciment may be determined by the apparatus and method of this invention.

EXAMPLE II

This example describes a test for Human Chorionic Gonadotropin (HCG) to determine pregnancy.

75 microliters of anti-HCG/latex bead reagent suspension (HWD) was pipetted into ten image cells loaded in a magazine assembly as hereinbefore described. Two cells were used as the control by adding 25 microliters of urine; one with known reactivity; and the other with unknown reactivity. The remaining image cells were charged each with 25 microliters of the test specimen. The magazine assembly was then incubated by slow rotation at 28° C. for eight minutes and their contents evaluated by the apparatus and method described herein. The results are shown in Table II below.

TABLE II

| Sample Number | Machine Score, Agglutination Units (Area) | Titer (HCG) Intl. Units (IU) |
|---|---|---|
| 1 (control) | 1627 | 2.5 |
| 2 (-control) | 0 | — |
| 3 | 1493 | 2.0 |
| 4 | 122 | 0.1 |
| 5 | 22 | 0.06 |
| 6 | 0 | — |
| 7 | 1400 | 1.5 |
| 8 | 3 | — |

While the foregoing invention has heretofore been described in detail with certain degrees of particularity, it must nevertheless be understood that numerous changes and/or modification may be made in the method or the apparatus which are obvious to those skilled in the art. Such changes and/or modifications, however, are still within the scope and contemplation of this invention.

What is claimed is:

1. An apparatus for use in connection with immunological reactions, said apparatus comprising:
   (a) a carriage assembly defined by front and rear walls and by side walls, said carriage assembly comprising a plurality of spaced, axially-disposed compartments between said side walls,
   (b) an image cell in each of said compartments, each image cell comprising two opposed, parallel, planar surfaces wherein each of said surfaces includes a generally circular groove so that when said surfaces are bonded together, said circular grooves define a reaction cell, and aperture in one of said grooves for introducing biological fluid and reagent into said reaction cell,
   (c) means for engaging with and biasing each of said image cells partially out of its respective compartment and into an optical path,
   (d) a light source for directing beams of light through said reaction cell,
   (e) an image sensor comprising a photosensitive surface consisting of photosensor elements,
   (f) an imaging lens for focusing the light beams transmitted through said reaction cell onto said image sensor on which dark images corresponding to agglutinated particles in the reaction cells are formed, and
   (g) means for determining the total dark imaged area on the surface of said image sensor.

2. An apparatus as in claim 1 wherein said carriage assembly includes at least two compartments.

3. An apparatus as in claim 1 wherein both said surfaces of said image cells are made of a transparent material.

4. An apparatus as in claim 2 wherein both said surfaces of said image cells are made of a transparent material.

5. An apparatus as in claim 3 wherein one of said surfaces is made of a transparent material and the other surface is made of a translucent material.

6. An apparatus as in claim 4 wherein one of said surfaces is made of a transparent material and the other surface is made of a translucent material.

7. An apparatus as in claim 1 wherein said means for engaging with and biasing each said image cell is a caliper means.

8. An apparatus as in claim 2 wherein said means for engaging with and biasing each said image cell is a caliper means.

9. An apparatus as in claim 3 wherein said means for engaging with and biasing each said image cell is a caliper means.

10. An apparatus as in claim 4 wherein said means for engaging with and biasing each said image cell is a caliper means.

11. An apparatus as in claim 5 wherein said means for engaging with and biasing each said image cell is a caliper means.

12. An apparatus as in claim 6 wherein said means for engaging with and biasing each said image cell is a caliper means.

13. An apparatus as in claim 1 wherein said means for determining the total dark imaged area on the surface of said image sensor is an electronic means.

14. An apparatus as in claim 2 wherein said means for determining the total dark imaged area on the surface of said image sensor is an electronic means.

15. An apparatus as in claim 3 wherein said means for determining the total dark imaged area of the surface of said image sensor is an electronic means.

16. An apparatus as in claim 4 wherein said means for determining the total dark imaged area on the surface of said image sensor is an electronic means.

17. An apparatus as in claim 5 wherein said means for determining the total dark imaged area on the surface of said image sensor is an electronic means.

18. An apparatus as in claim 6 wherein said means for determining the total dark imaged area on the surface of said image sensor is an electronic means.

19. An apparatus as in claim 7 wherein said means for determining the total dark imaged area on the surface of said image sensor is an electronic means.

20. An apparatus as in claim 8 wherein said means for determining the total dark imaged area on the surface of said image sensor is an electronic means.

21. An apparatus as in claim 9 wherein said means for determining the total dark imaged area on the surface of said image sensor is an electronic means.

22. An apparatus as in claim 10 wherein said means for determining the total dark imaged area on the surface of said image sensor is an electronic means.

23. An apparatus as in claim 11 wherein said means for determining the total dark imaged area on the surface of said image sensor is an electronic means.

24. An apparatus as in claim 12 wherein said means for determining the total dark imaged area on the surface of said image sensor is an electronic means.

25. An image cell for fluid reactants, said image cell comprising a pair of opposed, parallel planar surfaces bonded to each other, a generally circular indentation in each of said opposed surfaces so as to define a reaction cell, and an aperture in one of said indentations for introducing the fluid reactants into said reaction cell, wherein said indentations are sufficiently recessed so as to permit the fluid reactants to freely move within said cell while said cell is rotated and wherein said reactants remain confined without issuing from said cell during such rotation.

26. An image cell as in claim 25 wherein one of said surfaces are made from a transparent material.

27. An image cell as in claim 25 wherein one of said surfaces is made from a transparent material and the other surface is made of a translucent material.

28. An image cell as in claim 25 further including a generally cylindrical member attached on the inner face of one of said circular indentations for focusing an optical system on the mid-plane in the reaction cell.

29. An image cell as in claim 26 further including a generally cylindrical member attached on the inner face of one of said circular indentations for focusing an optical system in the mid-plane in the reaction cell.

30. An image cell as in claim 27 further including a generally cylindrical member attached on the inner face of one of said circular indentations for focusing an optical system on the mid-plane in the reaction cell.

* * * * *